United States Patent
Hinata et al.

[11] Patent Number: 5,900,945
[45] Date of Patent: May 4, 1999

[54] CHECK DETECTOR IN NECK AND FINISHED PORTION OF MOLDED BOTTLE

[75] Inventors: Kunio Hinata; Yuich Kawakita, both of Yokohama; Hitoshi Suzuki, Fukaya, all of Japan

[73] Assignees: Precision Co., Ltd., Yokohama; Nippon Glass Co., Ltd., Tokyo, both of Japan

[21] Appl. No.: 08/713,348

[22] Filed: Sep. 13, 1996

[30] Foreign Application Priority Data

Sep. 13, 1995 [JP] Japan ................................. 7-271693

[51] Int. Cl.⁶ ...................................................... G01N 21/90
[52] U.S. Cl. ........................ 356/428; 356/240; 356/237; 250/223 B
[58] Field of Search ................................... 356/428, 240, 356/237; 250/223 B

[56] References Cited

U.S. PATENT DOCUMENTS

| | | |
|---|---|---|
| 4,208,130 | 6/1980 | Caloyannis et al. |
| 4,213,042 | 7/1980 | Beach et al. |
| 4,293,219 | 10/1981 | Marcel. |
| 4,498,003 | 2/1985 | Johannes. |
| 4,701,612 | 10/1987 | Sturgill ..................... 356/240 |
| 5,536,935 | 7/1996 | Klotzsch ................... 356/240 |
| 5,610,391 | 3/1997 | Ringlien ................... 356/240 |

FOREIGN PATENT DOCUMENTS

| | | |
|---|---|---|
| 2042164 | 9/1980 | European Pat. Off. |
| 0303175 | 2/1989 | European Pat. Off. |
| 3815539 | 11/1989 | Germany. |

OTHER PUBLICATIONS

Patent Abstracts of Japan, vol. 017, No. 105, Mar. 3, 1993 & JP-A-04 294262, Oct. 19, 1992, abstract.

Patent Abstracts of Japan, vol. 95, No. 004, & JP-A-07 103915, Apr. 21, 1995, abstract.

*Primary Examiner*—Frank G. Font
*Assistant Examiner*—Reginald A. Ratliff
*Attorney, Agent, or Firm*—Townsend&Banta

[57] ABSTRACT

A check detector is provided for the neck and finished portions of a bottle which comprises a rotating means which is capable of rotating an inspection bottle; a plurality of emitters and a plurality of receivers arranged on an approximately hemispherical fixture arranged around the neck and finished portions of an inspected bottle as a center; means for obtaining N×M data per single scan against the inspected bottle, wherein N is a number of emitters, and M is a number of receivers; means for assorting the data obtained; and means for differentiating the data. Setting of job change depending on bottle types can be conducted automatically, and detecting checks in the neck and finished portions of a bottle can be conducted overall with no relation to the portion and type of defects. Detecting of a bubble, a contaminant, a chipped and unfilled thread and deformation which are known defects in the neck and finished portions of a bottle can be achieved. Further, assorting defects into both portions and type can be achieved to improve the quality control.

5 Claims, 5 Drawing Sheets

CHECK DETECTOR IN NECK AND FINISHED PORTION OF MOLDED BOTTLE

BACKGROUND OF THE INVENTION

The present invention is directed to a check detector in the neck and finished portions of containers such as bottles in a bottle manufacturing or filling line. The invention more specifically concerns such a method which can readily be automated.

Conventionally, in a bottle manufacturing or filling line, detection of checks in neck and finish portion of a bottle was primarily carried out by visual inspection, or by setting visually emitters (a) and receivers (b), according to the types of bottles and defects or checks.

The emitters (a) and receivers (b) occupy a plurality of inspection stations depending on the portion to be inspected.

Further, in another system, detection of checks in neck and finished portions of a bottle was carried out by using a plurality of fixed light to illuminate the neck and finished portions of bottle, and making a known window to the inspected portions by a CCD camera.

However, it is impossible to accurately visually detect defects. In the above method of setting visually a plurality of emitters depending on the type of checks, it is impossible to detect where the defects exist. Further, it is impossible to detect all kind of checks in neck and finished portions of a bottle. Further, in changing a job of detection of a molded bottle, it takes a long time to set emitters and receivers, etc.

There is a further problem in the above conventional inspection method by a CCD camera. Although the conventional method is effective in detecting vertical checks, horizontal checks along the horizontal screw of a bottle result in the detection sensitivity below. Further, in changing the detection job, re-setting of cameras, lights and sensitivities is required.

SUMMARY OF THE INVENTION

Overcoming the above drawbacks, the present invention provides a check detector which is capable of detecting checks which previously were difficult to detect, and which does so continuously, stably and at a low cost.

In order to achieve the above object, the present invention is directed to a check detector for the neck and finished portions of a bottle which comprises:

a known rotating means which is capable of rotating an inspection bottle;

a plurality of emitters and a plurality of receivers arranged on an approximately hemispherical fixture arranged around the neck and finished portions of an inspected bottle as a center;

means for obtaining N×M data per single scanning of an inspected bottle, wherein N is a number of an emitter, and M is a number of receiver;

means for assorting the data obtained; and means for differentiating the data.

In the check detector of the present invention, the judge value of the differentiation level is automatically set for a good bottle in changing a job of manufacturing a bottle, using the obtained judge value of a good bottle, when inspection of the inspected bottle is conducted of N ×M per scan in full perimeter; and conducting an inspecting check of the neck and finished portions of an inspected bottle, under the same setting condition as the good bottle.

The present invention provides a check detector, which is capable of detecting a bubble, an contaminant, e.g., stones, a chipped, an unfilled thread and other deformation which are known defects in the neck and finished portions of a bottle, and a check detector which is capable of assorting defects to both parts and kinds, and capable of displaying and monitoring.

According to the present invention, setting of a job change, depending on bottle types, can be conducted automatically, and detecting checks in the neck and finished portions of a bottle can be conducted overall with no relation to the portion and type of defects. A bubble, a contaminant, a chipped and unfilled thread and deformation which are known defects in the neck and finish portions of a bottle can then be detected. Further, assorting defects into both portions and type can be achieved to improve quality control.

Figure 1:
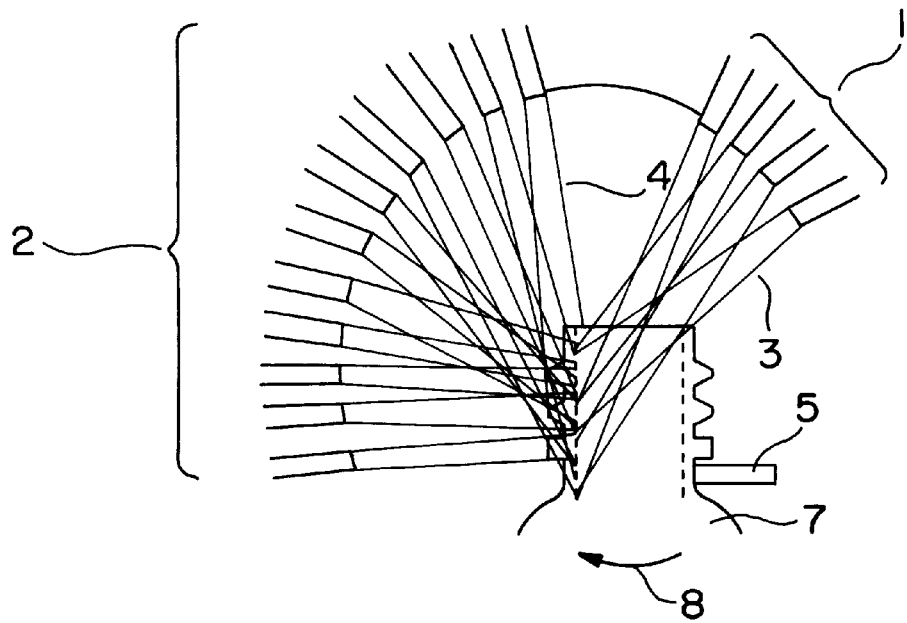
FIG. 1 is an illustration showing positions of emitters, receivers and area of emitter and receiver lights in an embodiment of the present invention.

Each of the items shown in the drawings is listed below as follows:

1 position of emitter
2 position of receiver
3 emitting line
4 receiving line
5 roller receiving bottle rotation
6 bottle rotation roller
7 bottle to be inspected
8 direction of bottle rotation
9 fixture head
11 emitter
12 receiver
13 starwheel
14 height adjuster
15 right and left adjuster
16 front and rear adjuster
17 receiver lens
18 receiver semi-condenser
19 receiver amplifier
20 receiver cable
21 multiplex A/D converter circuit
22 control logic circuit
23 CPU 24 screen
25 emitter lens
26 emitter semiconductor
27 emitter cable
28 to 37 emitter No. 1 to No. 10
38 receiving timing
39 receiving timing of the first scan
40 timing of the second scan
41 inspection area of Nth scan
42 inspection area of the first scan
43 inspection area of the second scan
44 inspection area of the third scan
45 machine rotation clock
46 in inspecting
47 inspection result
48 inspection processing
49 bottle stillness-rotation timing
50 bottle stillness-rotation end timing
51 inspection result out put timing
58 Power On
59 initialize (1)
60 Off Line
61 Off Line process
62 initialize (2)
63 individual emitter screen process
64 defect detection monitoring process
65 filing process
66 base date of a receiver sensor
67 CP parameter
68 defect level data
69 slice parameter
70 On Line start
71 signal comparison under inspection (1)
72 signal processing
73 signal comparison under inspection (2)
74 data assorting process
75 deferential calculus process
76 threshold comparison process
77 distinguishing defect process
78 inspection result process
79 screen display process
80 loop (1)
81 loop (2)
82 loop (3)
83 scan data
84 number of a good bottle
85 number of a defected bottle
86 total number of bottle inspected
87 number of horizontal checks
88 number of vertical checks
89 number of emitters
90 number of receiver
91 ratio of detecting of defection

DESCRIPTION OF THE PREFERRED EMBODIMENTS

The present invention is directed to a check detector for the neck and finished portions of a bottle which comprises:

a known rotating means which is capable of rotating an inspection bottle;

two or more, preferably from 2 to 30, most preferably about 20 emitters and two or more, preferably from 2 to 120, most preferably about 60 to 70 receivers arranged on an approximately hemispherical fixture arranged around the neck and finished portions of an inspected bottle as a center;

means for obtaining N×M data per single scan at each inspected point on the inspected bottle, wherein N is the number of emitters, and M is the number of receivers;

means for making bright processing around the full perimeter in an interval of constant distance, for example, from 0.1 to 10 mm;

means for assorting the data obtained; and means for differentiating.

The term "making bright processing" means obtaining a receiving light, and the term "inspected point" means an area where emitting and receiving lights are focused on an inspected bottle during one scan.

When the number of inspected points in the full perimeter of an inspected bottle is N and the number of scans is L, data having a number of L×N×N is obtained.

The data is assorted and then the data is differentiated to detect a changing point of light and darkness, and the quantity of the change, as explained in detail in Example.

For a good bottle, the judge level of the differentiation level is automatically set for such a level that the quantity or amount of change does not exceed the judge level of the differentiation level, then a check is not detected. The "judge level of the differentiation level" means a value which is differentiated and a predetermined value with a fixed margin. The judge level of the differentiation level is predetermined to zero at the initial condition, and the judge level increases higher according to the flow of good bottles.

For a defective bottle being checked, under the same setting conditions as a good bottle, a check is detected, since some of the differentiation data of N×M channels exceeds the judge level of the differentiation level. The term "differentiation process" means a known differentiation process.

In the present invention, an interference between a plurality of emitters and receivers does not occur, since emissions are not simultaneous. Thus, detecting checks can be made exactly and with over-lappingly.

Similarly, detection of a bubble, a contaminant, a chipped and unfilled thread and deformation which are known defects in the neck and finished portions of a bottle can be detected, since in the present invention, the reflected light can be detected and changing of the light direction can be also detected.

Further, with respect to finished top surface, particularly, of the finished portion, a top surface line over finish, unfilled finish, over press finish and bubble on finish, etc., can also be detected.

Further, the check detector of the present invention is capable of assorting defects into both portions and types, and, therefore, users are capable of improving the quality control and are capable of raising the productivity. That is, against the N×M channels, a user is able to set the type of defects, and is then able to read the assorting of each count.

According to the present invention, inspection of checks of the neck and finished portions of a bottle can be conducted for all kinds of types and positions of defects.

Changing of a job can be done easily and quickly, since the emitters and receivers, etc., are fixed in the present invention and the sensitivity is automatically set in the present invention.

As for the emitters used in the invention, LED emitters are preferably used because of high speed emission. However, the type of emitters is not limited, and laser may be used in the present invention as the emitter.

As for the receivers used in the present invention, photo receivers are preferably used, however, the type of receiver which can be used is not limited. Any conventional device for receiving and detecting light may be used in the present invention.

The emitters and receivers used in the present invention can be either fixed or semi-fixed on a fixture, preferably positioned on an approximately hemispherical fixture, around an inspected bottle.

The position or arrangements of the emitters and receivers on the hemispherical fixture are not particularly limited so long as the distant between emitters (receivers) and the inspected bottle is approximately constant. However, preferably at least one emitter (receiver) is positioned on the opposite side of the other emitters on the same surface of the hemispherical fixture, as shown in the FIG. 2.

The setting of the sensitivity for determining a good bottle as good is conducted by evaluating the increase or decrease of the value of the differential level.

Further, the assorting of the defects to both positions and types can be achieved by detecting the position of the channels.

EXAMPLES

Preferred embodiments of the present invention will now be described in detail with reference to the attached drawings.

As shown in the FIG. 1, an inspected bottle 7 in the inspection position are rotating in the rotation direction shown at 8. A plurality of emitters are arranged in emitter position 1, and a plurality of receivers are arranged in the receiver position 2. The emission an receiving light is conducted in the area of emitting lines 3 and receiving lines 4.

Figure 2:
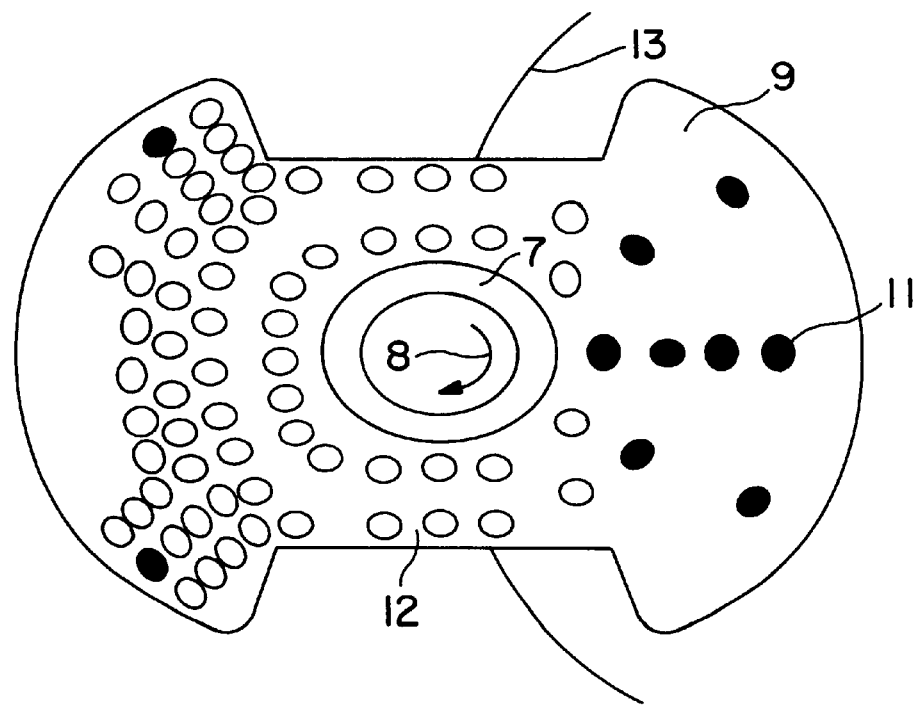
FIG. 2 is a detailed description of emitters and receivers on a fixture.

As shown in the FIG. 2, an inspected bottle 7 in the inspection position is positioned in starwheel 13 on the handling machine. Sensors of light are positioned on a fixture head 9, and 10 emitters and 64 receivers 12 are provided.

Figure 3:
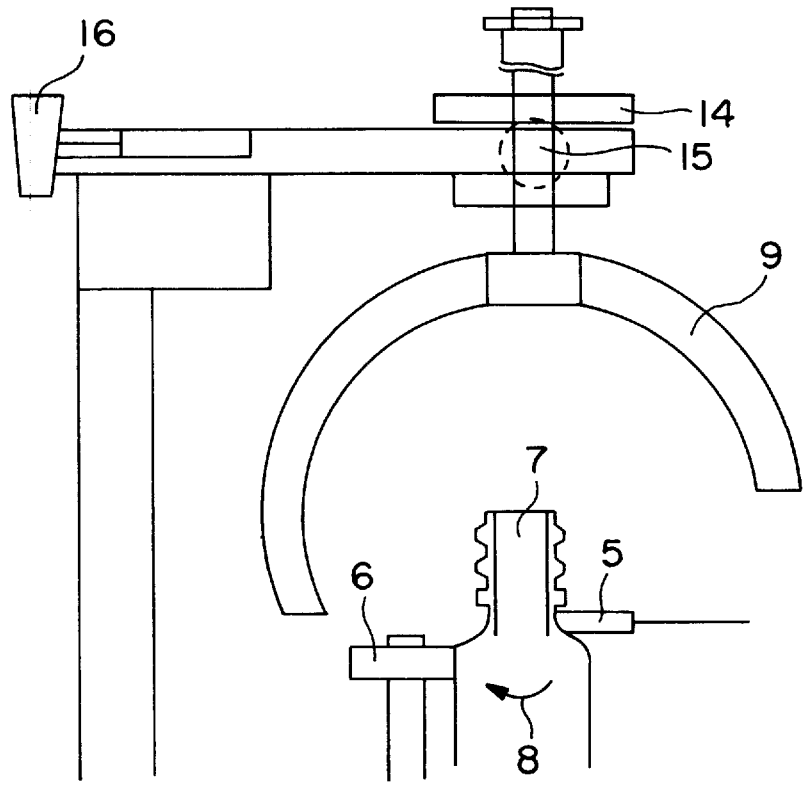
FIG. 3 is a cross sectional view illustrating dispositions of a fixture on a handling machine.

FIG. 3 shows a side view of the inspection machine. The fixture head 9 is set in a best position, using a height adjuster 14, a right and left adjuster 15 and a front and rear adjuster 16.

Figure 4:
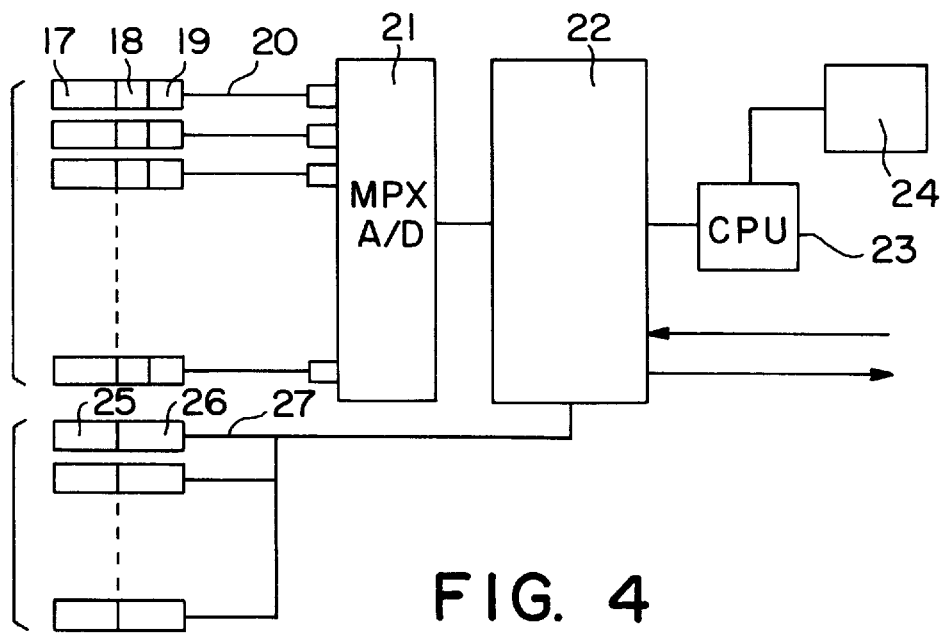
FIGS. 4 is a system block drawing illustrating an example of the present invention.
Figure 5:
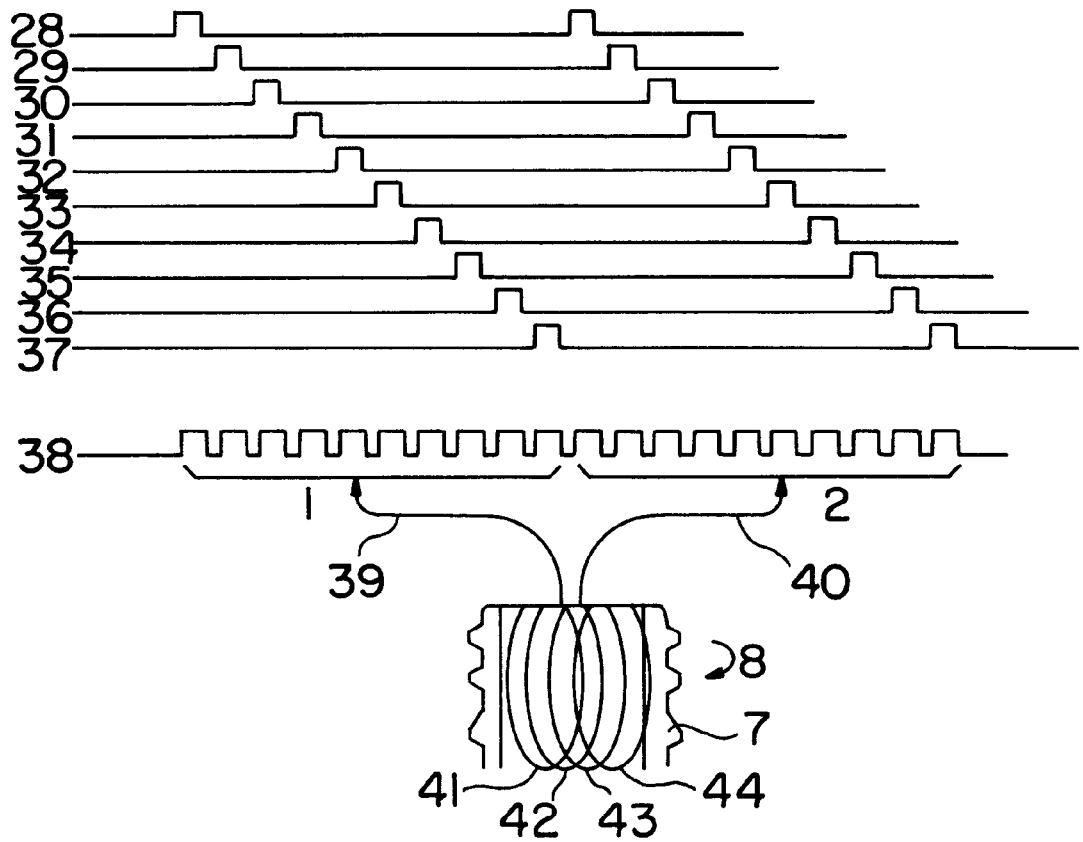
FIGS. 5 is an illustration showing timing sequences and an area of inspection.
Figure 6:
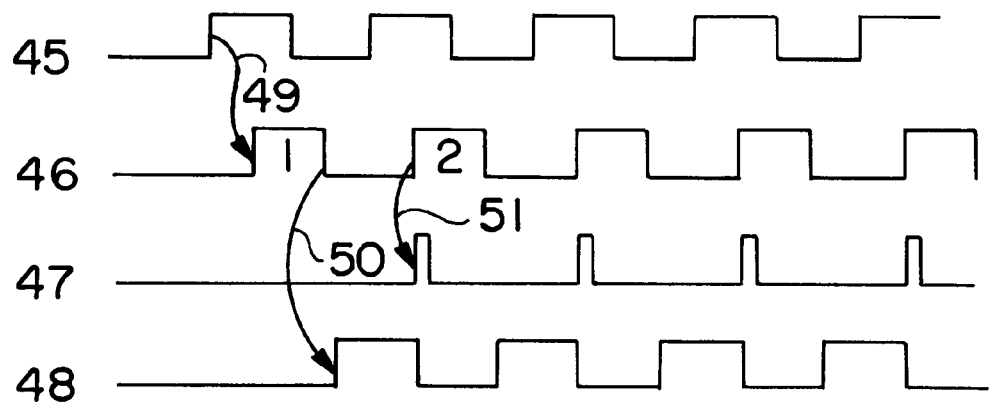
FIGS. 6 is an illustration showing a timing sequence of an inspection process on line.

FIG. 4 shows a system block chart of the present invention. The timing of emissions of the emitters No. 1–No. 10 which is composed of an emitter lens 25, an emitter semiconductor 26 and an emitter cable 27, are controlled by using a multiple A/D converter circuit 21.

The receivers No. 1–No. 64 which are composed of a receiver lens 17, a receiver semiconductor 18, a receiver amplifier 19 and a receiver cable 20 conduct a scanning of lights (1) every single emission with the timing indicated in receiving timing 38, from emitters No. 1 to No. 10.

The multiplex timing is controlled by a multiplex A/D converter circuit 21, then multiplex A/D conversion is conducted. The data of receivers are read into CPU 23 through the multiplex A/D converter circuit 21 and gathering of data of one scanning is finished.

The scanning is conducted fully around the bottle to gather the data. The receiving timing of the first scan 39 is at first scanning, the receiving timing of the second scan 40 is at second scanning, and the inspection area of the first scan 42 is at the first scanning and the inspection area of the second scan 43 is second scanning, 44 is at third scanning and 41 is Nth scanning.

An inspected bottle 7 is rotated in the direction of bottle rotation 8, Therefore, gathering of data is conducted fully around the bottle.

It is understood in the timing with the handling machine (FIG. 1), that one period of the machine rotated clock 45 is one handling of a bottle. The data of the full around inspection of the bottle is gathered in the period of inspection 46. The inspection processing 48 is conducted in time prior to the next inspection (2), and the inspection results 47 are output at the top of the inspection (2). In this case, when the bottle is a defective bottle, an exhausting signal is output.

Figure 7:
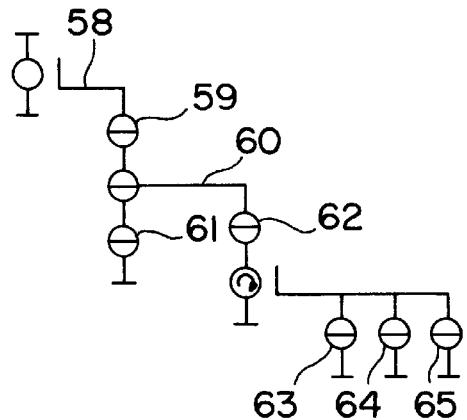
FIGS. 7 is a flow chart showing an out line of procedure an example of the present invention.

FIG. 7 illustrates the outline of soft ware of CPU 23. The preparation of the system motion is conducted by the operation of the initializing (1) 59 by Power On 58. Next, if the selection if Off Line 60, the preparation of Off Line operation is conducted by the treatment of initializing (2) 62 of Off Line to a wait the selection of the operation. In the Off Line operation, there are individual emitter screen process 63, defect detection monitoring process 64 and filing process 65, which are performed by the selection. If the selection is On Line, Off Line process 61 is conducted.

Figure 8:
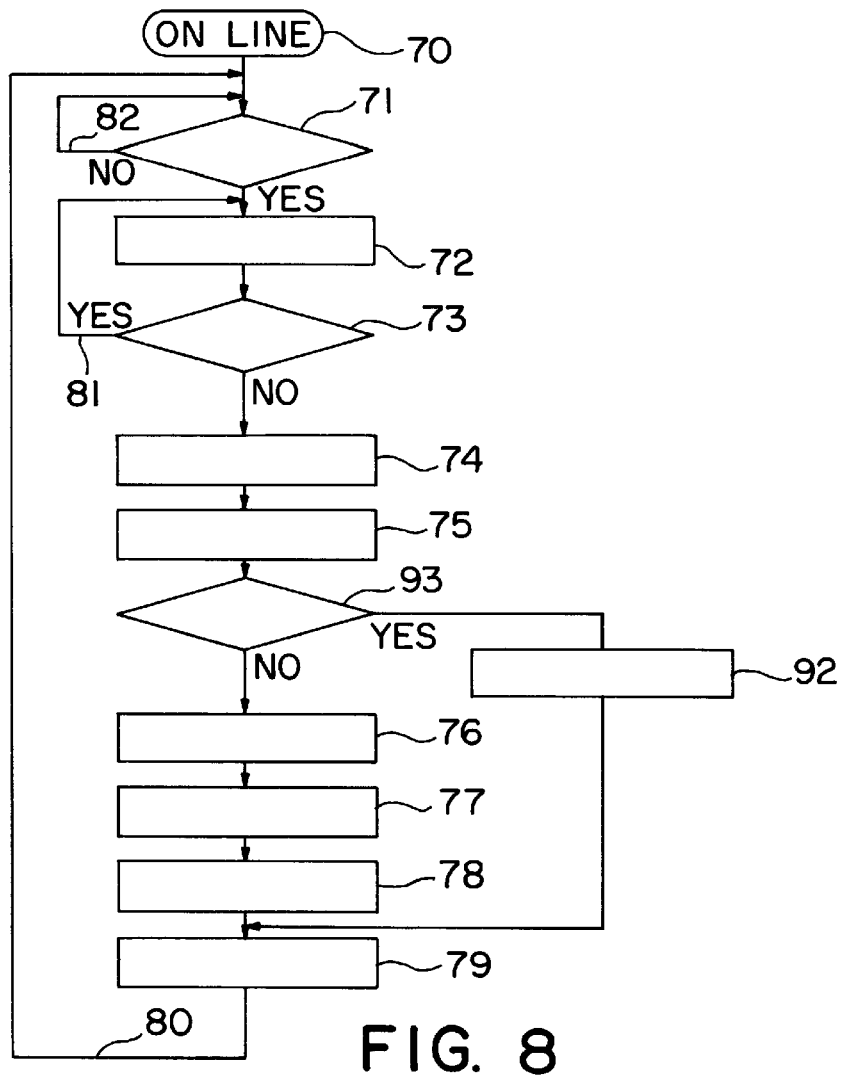
FIG. 8 is a flow chart showing operation process on line.

FIG. 8 shows a flow chart of Off Line process 61. The operation is started by One Line start 70. During the inspection, the inspection 46 is recognized by signal comparison under inspection (1) 71, and the scanning of emission and receiving are started. At that time, CPU reads 60 of data of light per one emitter, 10 emitter's data per one scanning, fully around the bottle, about 100 scans which depend on the speed of the rotation of the bottle by receiving signal processing 72.

Next, by data assorting process 74, the data in emitters and receivers obtained by approximately 100 scans are assorted to each channels to obtain assorted data by each 10×60 channels. These procedures are called by data assorting.

Then, the data is conducted by differential calculus process 75 over each scanning to calculate any changing amount of the received light data. For a good bottle, as the judge level of the differentiation level is automatically set by automatic set process (92) in such a level that the quantity of changing does not exceed the judge level of the differentiation level, then a check is not detected. The judge level of the differentiation level is predetermined to zero at the initial condition, and the judge level increases higher according to the flow of good bottles.

Then, when the calculated amount exceeds the threshold value set by threshold comparison process 76, the bottle is determined as a defected bottle, and by determining of defect process 77, the bottles are classified according to the pre-determined defect classification.

An NG signal is output by an inspection result process 78, then the defected bottle is exhausted. An NG signal is displayed by the screen displaying process 79. Thereafter, the next inspected bottle is waited in loop (1) 80.

Figure 9:
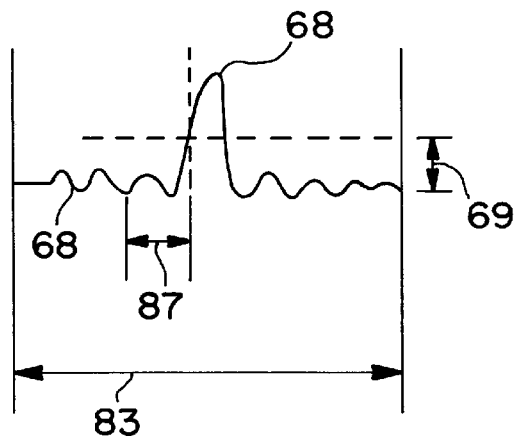
FIGS. 9 is an drawing showing a differential process.

FIG. 9 illustrates differential processing and the threshold process. The scanning data 83 is a data obtained after assorting of data in about 100 scans from one emitter and one receiver of above 10 emitters and 64 receivers. The item 68 shows defect level data 68, and the item 66 shows receiver sensor base data and the item 67 shows CP parameter, that is, a differential comparison width. The CP parameter is usually set from 1 to 10. The CP parameter is a parameter which shows that the deference is found with how many previous scanning.

The slice parameter 69 which is set in the range from 5 to 100, is used as a threshold value. When the amount exceeds the threshold value (68), the bottle is determined to be a defected bottled. These procedures are called by differentiating.

Figure 10:
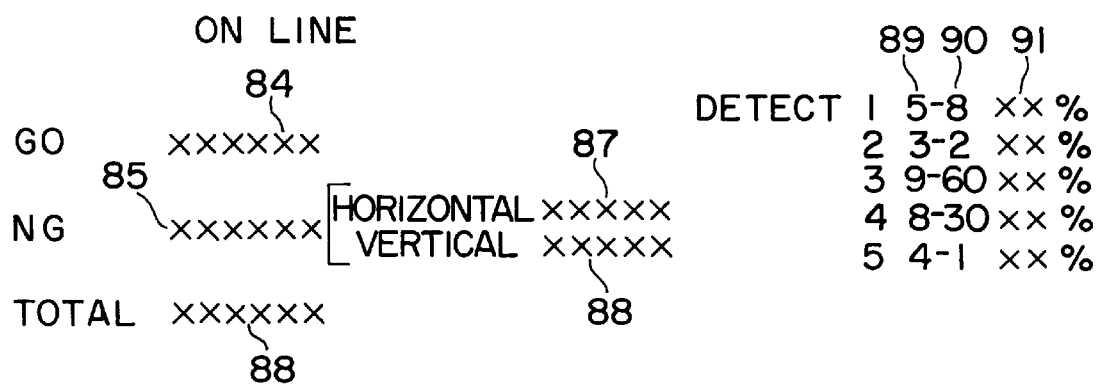
FIGS. 10 shows a screen on line.

FIG. 10 shows the screen at the time of On Line. The number of good bottles 84, the number of defective bottles 85 and total number of bottles inspected 86 are monitored. The number of vertical checks 87 and number of horizontal checks 88 out of the number of defected bottles 85 are also displayed.

Further, the number of the defective bottles is displayed for every emitter and receiver.

The emitter's number 89, receiver's number 90 and the ratio of detection of defection 91 are important data for investigating the reason for the defection, by gathering the data of defecting portions, as well as by feed back to the line.

According to the present invention, the method of defecting of checks in the neck and finished portions of a molded bottle can be improved, and the operation time of job change for every bottle type is shortened considerably.

Further, by displaying data of defection type precisely, analysis and countermeasure can be taken rapidly. The improvement of the productivity and automation can be achieved by these effects of the invention.

What is claimed is:

1. A check detector in the neck and finished portion of a bottle which comprises:

rotating means for rotating an inspection bottle;

a plurality of emitters and a plurality of receivers arranged on an approximately hemispherical fixture arranged around the neck and finished portion of an inspected bottle as a center;

means for obtaining N * M data per single scanning against said inspected bottle, wherein N is a number of emitters, and M is a number of receivers;

means for assorting the data obtained; and means for differentiating the data obtained from scanning a good bottle, wherein a judge value of the differentiation level is automatically set by scanning a good bottle and, obtaining N * M per single scanning in full perimeter for said good bottle, and then, conducting an inspection check of the neck and finished portions of an inspected bottle, under the same setting condition as the good bottle.

2. The check detector according to claim 1, further comprising means for detecting a bubble, an containment, a chipped and unfilled thread and deformation in the neck and finished portions of an inspected bottle.

3. A check detector in the neck and finished portion of a bottle which comprises:

rotating means for rotating an inspection bottle;

a plurality of emitters and a plurality of receivers arranged on an approximately hemispherical fixture arranged around the neck and finished portion of an inspected bottle as a center;

means for assorting defects to both parts and kinds;

means for displaying and monitoring of said inspected bottles;

means for obtaining N * M data per single scanning against said inspected bottle, wherein N is a number of emitters, and M is a number of receivers;

means for assorting the data obtained; and means for differentiating the data obtained from scanning a good bottle.

4. The check detector according to claim 1, further comprising means for assorting defects to both parts and kinds, and means for displaying and monitoring said inspected bottles.

5. A check detector in the neck and finished portion of a bottle which comprises:

rotating means for rotating an inspection bottle;

a plurality of emitters and a plurality of receivers arranged on an approximately hemispherical fixture arranged around the neck and finished portion of an inspected bottle as a center;

means for detecting a bubble, a contaminant, a chipped and unfilled thread and deformation in the neck and finished portions of an inspected bottle;

means for assorting defects to both parts and kinds;

means for displaying and monitoring of said inspected bottles;

means for obtaining N * M data per single scanning against said inspected bottle, wherein N is a number of emitters, and M is a number of receivers;

means for assorting the data obtained; and means for differentiating the data obtained from scanning a good bottle.

* * * * *